United States Patent
Poyhtari et al.

(10) Patent No.: US 9,700,760 B2
(45) Date of Patent: Jul. 11, 2017

(54) EXERCISE-RELATED DEVICE DATA SENT INDIRECTLY THROUGH INTERMEDIARY DEVICE TO FIRST REMOTE SERVER OR DIRECTLY SENT TO SECOND REMOTE SERVER FOR PROCESSING

(71) Applicant: Polar Electro Oy, Kempele (FI)

(72) Inventors: Petteri Poyhtari, Kempele (FI); Simo Rantanen, Jyvaskyla (FI)

(73) Assignee: POLAR ELECTRO OY, Kempele (FI)

( * ) Notice: Subject to any disclaimer, the term of this patent is extended or adjusted under 35 U.S.C. 154(b) by 732 days.

(21) Appl. No.: 14/095,552

(22) Filed: Dec. 3, 2013

(65) Prior Publication Data
US 2014/0156038 A1    Jun. 5, 2014

(30) Foreign Application Priority Data
Dec. 4, 2012  (EP) ................................ 12195453

(51) Int. Cl.
A61B 5/00   (2006.01)
A63B 24/00  (2006.01)
G06F 19/00  (2011.01)

(52) U.S. Cl.
CPC ...... *A63B 24/0062* (2013.01); *G06F 19/3412* (2013.01); *G06F 19/3481* (2013.01); *G06F 19/3406* (2013.01)

(58) Field of Classification Search
CPC .... G06F 3/00; G06F 19/3418; G06F 19/3412; G06Q 50/00; A63B 24/0062
(Continued)

(56) References Cited

U.S. PATENT DOCUMENTS 6,605,038 B1 * 8/2003 Teller .................... A61B 5/411
                                                    128/904
6,668,376 B1   12/2003 Wang et al.
(Continued)

FOREIGN PATENT DOCUMENTS

WO     02/00111 A1   1/2002

OTHER PUBLICATIONS

Search Report, European Application No. EP 12195453, dated May 30, 2013, 2 pages.

*Primary Examiner* — Tammara Peyton
(74) *Attorney, Agent, or Firm* — Hoffmann & Baron, LLP (57) ABSTRACT

A method includes executing a data processing application including a static part for performing at least the following functions: determining at least one identifier of an exercise monitoring device which is connected to the computing device, wherein the connected exercise monitoring device comprises exercise-related data; indicating the determined at least one identifier to a first server over a network, wherein the first server stores operational attributes for a plurality of different exercise monitoring devices; and receiving information indicating operational attributes associated with the connected exercise monitoring device from the first server, wherein the indicated operational attributes form an exercise monitoring device-specific dynamic part of the data processing application. The method also includes performing, by the dynamic part, at least one operation to the exercise-related data on the basis of the indicated operational attributes associated with the connected exercise monitoring device.

18 Claims, 5 Drawing Sheets

(58) Field of Classification Search
USPC .................... 713/1, 2; 710/8–10, 36, 17–19; 709/220–223; 705/2
See application file for complete search history.

(56) References Cited

U.S. PATENT DOCUMENTS

| | | | |
|---|---|---|---|
| 8,152,693 B2 * | 4/2012 | Nurmela | A63B 24/0084 482/8 |
| 2002/0083228 A1 | 6/2002 | Chiloyan et al. | |
| 2007/0136098 A1 | 6/2007 | Smythe et al. | |
| 2011/0179405 A1 * | 7/2011 | Dicks | G06F 8/61 717/168 |
| 2012/0182939 A1 | 7/2012 | Rajan et al. | |
| 2012/0259652 A1 * | 10/2012 | Mallon | G06F 19/3418 705/2 |
| 2015/0081763 A1 * | 3/2015 | Sipola | A61B 5/00 709/203 |

\* cited by examiner

FIG. 8

EXERCISE-RELATED DEVICE DATA SENT INDIRECTLY THROUGH INTERMEDIARY DEVICE TO FIRST REMOTE SERVER OR DIRECTLY SENT TO SECOND REMOTE SERVER FOR PROCESSING

CROSS-REFERENCE TO RELATED APPLICATIONS

This application claims priority to European Application No. 12195453.1, filed 4 Dec. 2012, which is incorporated by reference herein in its entirety.

BACKGROUND

Field

The invention relates generally to transferring and processing exercise-related data comprised in an exercise monitoring device.

Description of the Related Art

Nowadays people often want to see the results of their physical exercises not only in a performance monitor, such as in a wrist watch, but also on a screen of a computer, a laptop, a mobile phone, etc. This requires the computing device to comprise appropriate software. However, one type of software may only be able to appropriately process exercise-related data with respect to a certain type of performance monitor or exercise monitoring device. When the user buys another performance monitor, new software may need to be installed or at least the old software may need to be updated. This may be a time consuming and frustrating task.

SUMMARY

According to an aspect of the invention, there are provided apparatuses as specified in claims 1 and 17.

According to an aspect of the invention, there is provided a method as specified in claim 15.

According to an aspect of the invention, there is provided a computer program product as specified in claim 16.

According to an aspect of the invention, there is provided a computer-readable distribution medium carrying the above-mentioned computer program product.

According to an aspect of the invention, there is provided an apparatus comprising processing means configured to cause the apparatus to perform any of the embodiments as described in the appended claims.

According to an aspect of the invention, there is provided an apparatus comprising a processing system configured to cause the apparatus to perform any of the embodiments as described in the appended claims.

According to an aspect of the invention, there is provided an apparatus comprising means for performing any of the embodiments as described in the appended claims.

Embodiments of the invention are defined in the dependent claims.

BRIEF DESCRIPTION OF THE DRAWINGS

In the following, the invention will be described in greater detail with reference to the embodiments and the accompanying drawings, in which.

DETAILED DESCRIPTION

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

It is common to wear a personal training computer during an exercise. The personal training computer, or in general an exercise monitoring device, may be worn in the wrist of the user. The training computer may receive heart rate related information from a heart rate monitor, location specific information from a foot pod or from a global positioning system (GPS) receiver, cadence data from a corresponding monitoring device. pace/speed related data from the GPS/foot pod, etc. The training computer may store the data as exercise-related data which the user may use in post-analysis of the performed exercise. Such post-analysis may be at some level processed in the training computer, such as in a wrist computer. However, for a more accurate and in-depth analysis, the exercise-related data is typically transferred from the training computer/monitoring sensor to a web-based service, such as Polar Personal Trainer (PTT) service, located in a server of a network. The transfer of the data may be performed via a data processing application stored in and executed by a computer (PC), a laptop, a tablet, a mobile phone, a gym equipment or, in general, any other computing device capable to access the network. Such data processing application may be, for example, a WebSync or a WebLink-application provided by Polar Electro.

However, typically the data processing application is exercise monitoring device-specific. Here, the exercise monitoring device may mean a training computer, a stride sensor, a GPS receiver, a cadence sensor, mobile phone with exercise software or any other equipment capable of monitoring, storing and/or recording at least some data related to, associated with or applied during the exercise. Accordingly, the data processing application may need to store software for a plurality of exercise monitoring devices. This may make the data processing application large and to cause a significant load to the computing device applied by the client.

Further, acquiring a new performance/exercise monitoring device may require the old software installed in the computing device to be updated or re-installed with updated parameters. For example, a new exercise monitoring device may apply different coding or packing protocol for a specific performance metric, such as for heart rate variation. In order for the computing device to be able to perform process the specific performance metric correctly, an update of the data processing application may be needed. Such update may require downloading the new updated software from the service provider, such as from Polar Electro, and installing the downloaded software in the personal computing device. This may also comprise deleting the old software, such as the data processing application, from the computing device. Each of these may be a time consuming and a frustrating task requiring computational effort from the personal computing device. It should be noted that while a high-performance PC may be able to perform the tasks rather quickly, a mobile phone, a tablet, or any other limited performance computing device may struggle with such update-procedure.

Figure 1:
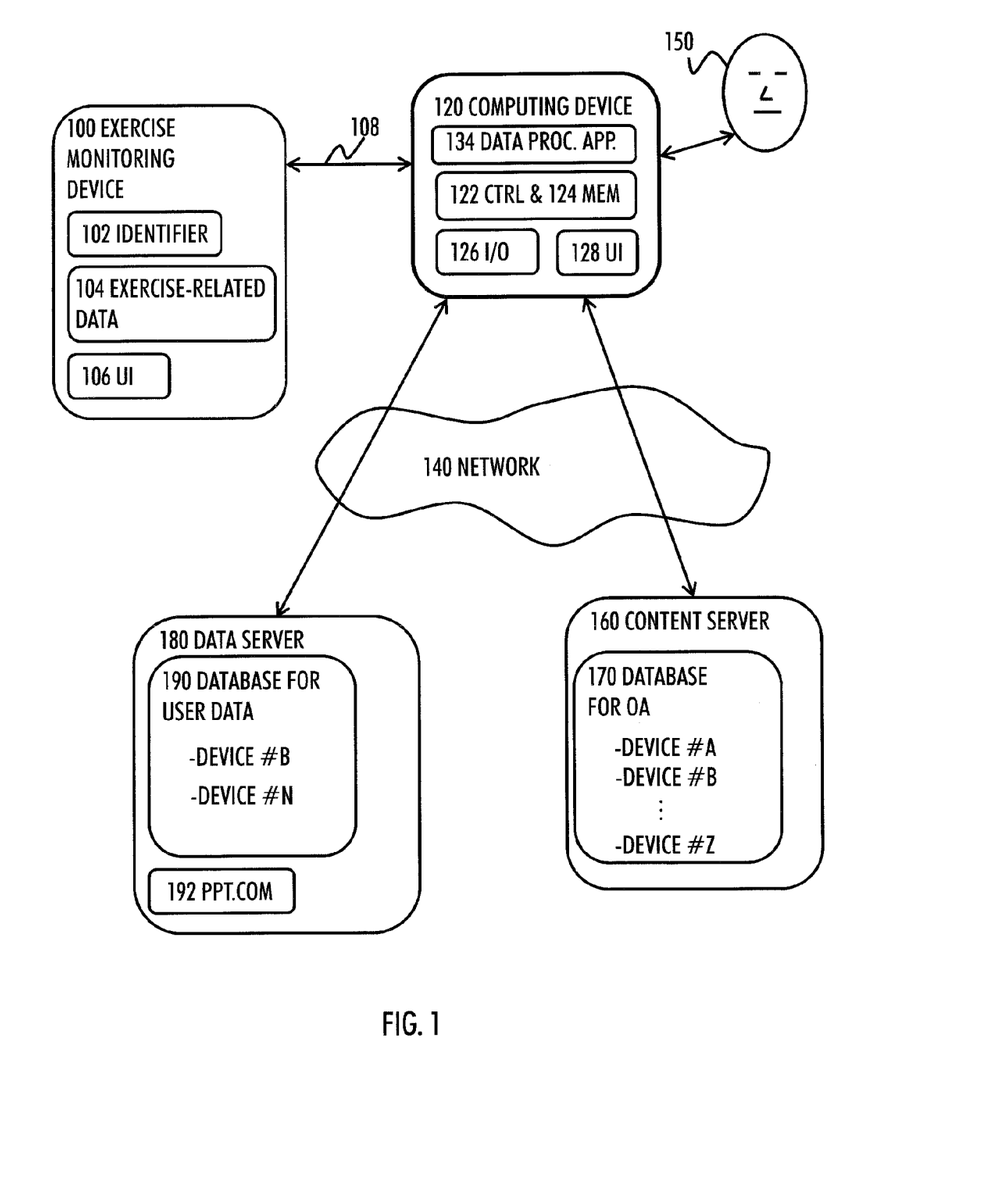
FIG. 1 presents a system according to an embodiment.

FIG. 1 shows a system in which the embodiments of the invention may be applicable to. The system may include the exercise monitoring device (EMD) 100, the computing device 120, a content server 160 and a data server 180. The EMD 100 may comprise identity information 102 for indicating the identity of the EMD 100, the exercise-related data 104, such as heart rate related information, speed/pace, calories consumed, etc., and a user interface 106 for enabling the user of the EMD 100 to control the device 100. The user of the EMD 100 may be the same as the user of the computing device 120, that is, the user 150. The user interface 106 may comprise, e.g., buttons, display, microphone, speakers, touch sensors, etc.

The computing device 120 may be a personal computing device or a shared computing device. In an embodiment, the computing device is integrated into an exercise equipment, such as a treadmill or a bicycle. The computing device 120 may comprise at least one processor 122 and at least one memory 124 including a computer program code (PROG). Further the computing device may comprise a data processing application 134.

Figure 3:
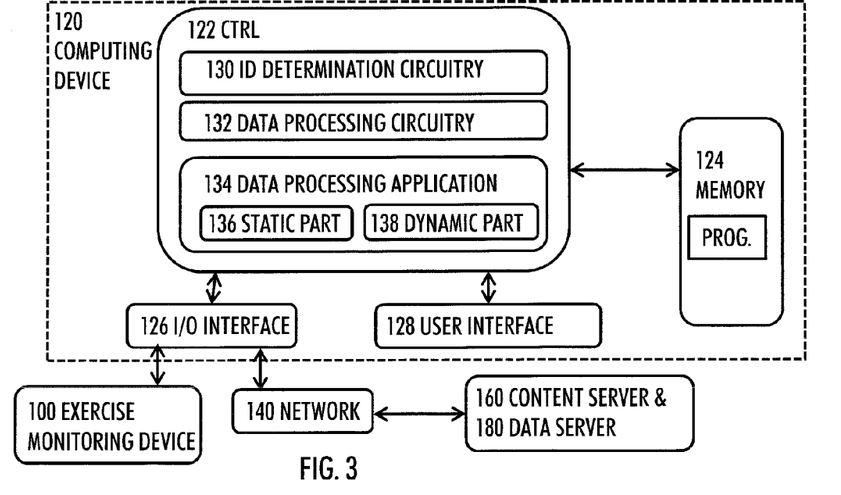
FIGS. 3 and 5 show apparatuses according to some embodiments.

FIG. 3 shows a more detailed illustration of the computing device 120. The computing device 100 may further comprise an input/output interface 126 (I/O) for receiving exercise-related data 104 from the EMD 100 and for outputting the exercise-related data 104 further, for example. The computing device 120 may also comprise a user interface 128 (UI) comprising, for example, at least one keypad, a microphone, a touch display, a display, a speaker, etc. for controlling the computing device 120.

The servers 160, 180 may be a part of the client-server computing model that acts as distributed application which may partition tasks or workloads between the provider of a resource or service, called the server 160, 180, and the service requester, such as the computing device 120. The server computer 160, 180 is a host that is running one or more server programs. The computing device 120 may, for example, request a server's content or a service function.

The data server 180 may store in a database 190 the exercise-related data 104 with respect to a plurality of users and with respect to a plurality of different EMDs 100 of the same or of different users. The data server 180 may comprise a database, for example, the Polar Personal Trainer (PPT) web service 192 to which clients (i.e. the users of the EMDs 100) may register to. The data server 180 may be responsible of performing the post analysis of the exercise-related data 104 once transferred to the data server 180, for example. Let us look at the functionalities of a content server 160 later.

Figure 2:
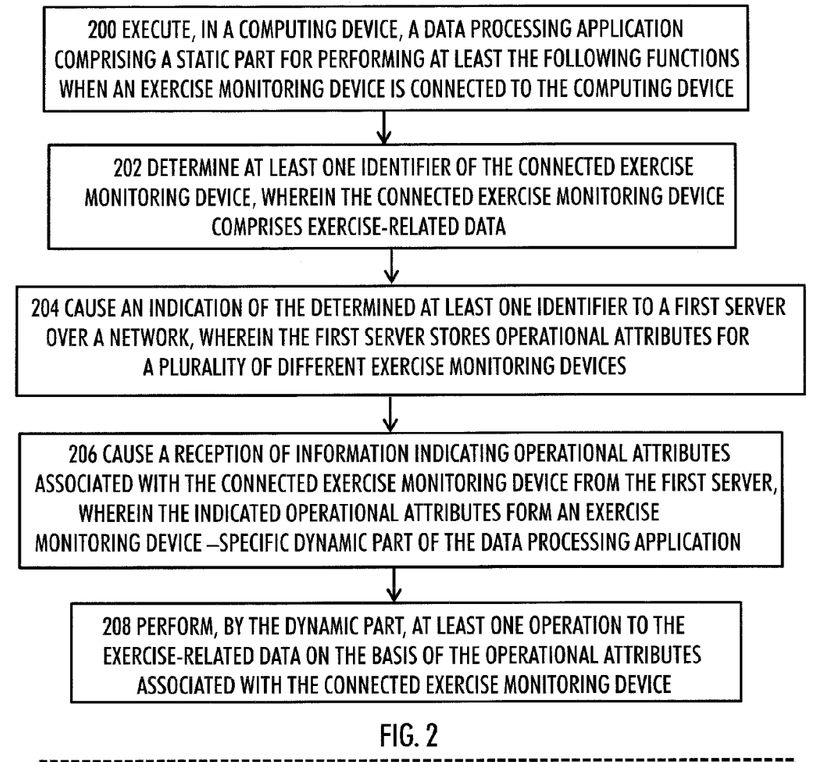
FIGS. 2, 4, 6 and 7 show methods according to some embodiments.

In order to avoid the time consuming and frustrating task of updating or re-installing the data process application 134 of the computing device 120 frequently, it is proposed, as shown in FIGS. 2 to 3, that the at least one memory 124 and the computer program code (PROG) are configured, with the at least one processor 122, to cause, in step 200, the computing device 120 to execute, in the computing device 120, the data processing application 134 comprising a static part 136 for performing certain steps/functions when an exercise monitoring device is connected to the computing device 120. The data processing application 134 may be executed when any EMD is connected to the computing device 120. The functionalities of the static part 136 do not depend on the type/model, etc. of the EMD that is connected to the computing device 120. The connection 108 between the exercise monitoring device 100 and the computing device 120 may comprise at least one the following: a cable, an infra-red (IR), a Bluetooth, wireless communication via a wireless network, a wireless communication utilizing electric and/or magnetic fields. As such, the computing device 120 may detect the EMD 100 upon plug-in of the cable, upon pairing of the Bluetooth protocol, upon detecting wireless transmission from the EMD 100, etc. The connection establishment may be also performed via a second I/O module coupled to the computing device 100 (not shown). An example I/O module may be an infra-red module, a FlowLink, a DataLink or a WindLink provided by Polar Electro. The module may be plugged in to a universal serial bus (USB), or any other communication port/interface of the computing device 120.

The static part 136 may then in step 202 determine at least one identifier 102 of the connected exercise monitoring device 100, wherein the connected EMD 100 comprises exercise-related data 104. In an embodiment, the identifier 102 comprises at least one of the following: the type of the connected EMD 100, the brand of the connected EMD 100, the model of the connected EMD 100, the serial number of the connected EMD 100, the age of the connected EMD 100, the manufacturer of the connected EMD 100, the firmware version of the connected EMD 100. For example, the type or brand of the EMD 100 may be Polar, whereas the model may be RS400, RCX5, FT40, etc. An example of the manufacturer may be Polar Electro. The age or the serial number may be important as this may indicate the software or firmware versions of the EMD 100, for example, unless they are given explicitly. The computing device 120 may request the EMD 100 to indicate the identifier 102 or the EMD 100 may transmit the identifier 102 to the computing device 120 without any explicit request. For example, during pairing of the devices 100, 120 according to the used communication protocol, the computing device 120 may acquire the identifier 102 of the EMD 100.

As said, the EMD 100 may include or the EMD 100 may store at least some exercise-related data 104. Such exercise-related data 104 may have been stored during one exercise or during several exercises or physical activities. The following is a non-limiting list of possible types of exercise-related data 104 available from the EMD 100: heart rate zones, heart rate samples, heart rate variation samples, fat consumption, calorie consumption, activity zones, activity samples, speed and/or pace samples, power samples, cadence samples, altitude samples, temperature samples, location samples, pedal index, left-right balance, running index, training load, galvanic skin response samples, fluid balance, skin temperature samples, music list. A certain model of the EMD 100 may comprise different types of exercise related data 104 than another model. For example, some EMDs may not be able to store location related GPS data, whereas some are able to do so. It should also be noted that the term "exercise-related data" may denote data produced on the basis of the performed physical exercise(s), such as heart rate samples, fat/calorie consumption, running index, training load, etc. Further, the term 104 may denote also data related to the exercise, such as configured heart rate zones for the person for the exercise, default heart rate zones available for use during the exercise, music tracks or music lists comprised in the EMD 100 and available for listening during the exercise. In other words, data that is not generated on the basis of or during the physical activity/exercise, but data that is available to be used during or for the benefit of the exercise.

In step 204, the computing device 120 may with the static part 136 indicate the determined at least one identifier 102 to a first server 160 via a network 140, wherein the first server 160 stores operational attributes for a plurality of different exercise monitoring devices. The network 140 may be any network providing connectivity to the content server 160, such as the Internet. The communication over the network may take place by applying TCP/IP and HTTP protocols. The first server 160 may be also called a content server as it comprises a database 170 including sets of operational attributes, each set associated with a different EMD (devices #A, #B, . . . #Z). By different EMD it is meant that the EMDs may vary in the type, brand, model, etc. It should be noted that the device #A may apply different operational attributes than the device #B, etc. This is why it may be important to store the "intelligence" needed by the computing device 120 in accessing the exercise-related data of different EMDs. The operational attributes may refer to the logic, configuration, functionality, and user interface layer settings of the data processing application 134 required for accessing the data 104 in the EMD 100, to mention only a few possible contents of the operational attributes.

It should be noted that in an embodiment, although the static part 136 of the data processing application 134 performs the ID protocol for determining the identifier 102 of the EMD 100, the computing device 120 may merely transmit the identifier 102 to the server 160 but it need not identify the EMD 100. The content server 160 may then identify the connected EMD 100 on the basis of the indicated identifier 102. This embodiment may allow a simpler data processing software/application 134 because it need not compare the determined identifier 102 to any database itself. In another embodiment, the static part 136 of the data processing application 134 also identifies the connected EMD 100 on the basis of the determined identifier 102 in addition to transmitting the identifier 102 to the server 160.

In step 206, the computing device 120, and more particularly the static part 136, receives information indicating the operational attributes associated with the currently connected exercise monitoring device 100 from the first server 160. The operational attributes may be also called operational parameters, data structures or data records, for example. The operational attributes may be indicated to the computing device 120 in a java script-format. As a result, the computing device 120 need not store the operational attributes for each and every type of exercise monitoring device, which reduces the used amount of memory 124 of the computing device 120. Instead, the computing device 120 may simply receive, from the server 160, the required operational parameters (e.g. the "intelligence") needed for processing or performing operations to the data 104 with respect the currently connected EMD 100.

The indicated operational attributes may then form or be applied in forming an exercise monitoring device-specific dynamic part 138 of the data processing application 134. In an embodiment, the static part 136 generates the dynamic part 138 on the basis of the indicated operational attributes. In another embodiment, the operational attributes comprise an executable packet which auto-generate such dynamic part 138 to the data processing application 134. It should be noted that receiving the required operational attributes from the server 160 may enable the data processing application 134 to be simpler and to cause significantly reduced amount of computational load to the computing device 120. Further, it should be noted that prior to receiving the operational attributes from the server 160, the computing device 120 may be unable to perform operations (such as process or transfer) to the exercise-related data 104 and/or to the EMD 100. That is, the data may be inaccessible to the computing device 120 prior to receiving the "intelligence" or "logic" from the server 160, that is, prior to generating the dynamic part 138 which is specific to the connected EMD 100. As will be described later, the computing device 120 may require the operational attributes in order to perform the at least one operation to the data 104, such as transfer of the data 104.

As one example advantage, the static part 136 of the data processing application 134 of the computing device 120 need not be updated or re-installed often because the operational attributes of the EMDs, which may require such update relatively often, are stored in the server 160. In this case it is enough that the server 160 is updated and this update may be invisible to the user 150 of the computing device 120. An update of the server 160 may be in order each time a new exercise monitoring device is brought to markets, for example. Also, an update may be needed when a software bug is detected in the software. In such case it is beneficial, from the point of view of the reputation/image of the software provider, to be able to fix the bug without the user 150 knowing anything about the update. This may further provide more reliable service by the service provider as the bar for making such updates is significantly lower when they are performed without the user 150 knowing. As the server 160 may be updated frequently, the dynamic part 138, which is formed on the basis of the operational attributes stored in the server 160, is always up-to-date and the end-user 150 may enjoy reliable and up-to-date service. Further, the use of different servers 160 and 180 for operational attributes and for data offers flexibility from the point of view of the service provider, for example.

A further advantage may be that the static part 136 of the data processing application 134 in the computing device 120 may be on all the time without any need to re-starting the application. This may be enabled because no update is needed to the static part 136 of the data processing application 134 which retrieves, the required tools for establishing the dynamic part 138, for accessing the data 104 and for working with the EMD 100.

In an embodiment, the static part 136 performs at least the said functions (i.e. the steps 202, 204, and 206) each time any exercise monitoring device is connected to the computing device 120. In this way, the dynamic part 138 is generated from the beginning each time any EMD is connected to the computing device 120 on the basis of the EMD-specific operational attributes retrieved from the server 160 by the static part 136. Thus, the dynamic part 138 may change each time the application 134 is used, depending on which EMD is connected to the computing device 120 and depending on updates performed for the server 160, for example. Even if the same EMD 100 is connected to the computing device 120 later, such as on the following day, the static part 136 of the data processing application 134 initiates the generation of the dynamic part 138 from the beginning by requesting the server 160 to respond with the correct operational parameters for the EMD 100. In other words, in an embodiment, the dynamic part 138 is deleted upon disconnecting the EMD 100 from the computing device 120. That is, the data processing application 134 or the computing device 120 does not store any dynamic parts 138 in the memory permanently. This may simplify the data processing application 134 significantly, as the basic functions caused by the static part 136 are the same each time any EMD is connected to the computing device 120 and the EMD-specific dynamic part 138 is formed from the start each time any EMD is connected to the computing device 120.

Yet one advantage due to the proposed solution may be that the users 150 of the computing devices 100 may generate skins or other software-related functions for the data processing application. These software-related functions may be transmitted to and stored in one of the servers 160/180. Other users 150 may then apply those software-related functions in their own computing devices 120.

In an embodiment, the computing device 120 requests the first server 160 to indicate the operational attributes associated with the connected exercise monitoring device 100 on the basis of the at least one identifier 102 upon connection of the exercise monitoring device 100 to the computing device 120. In this way, each time any EMD is connected to the computing device 120, the computing device 120 automatically requests the content server 160 to response with the correct operational attributes applied by or associated with the connected EMD 100. In this case the computing device 120 may acquire the operational attributes associated with the exercise monitoring device 100 directly from the information received from the content server 160.

In another embodiment, the computing device 120 may itself store a database X (similar to the database 170) comprising operational attributes for a plurality of EMDs. Then the computing device 120 may select the operational attributes from the sets of operational on the basis of the information received from the content server 160. In this case, the server 160 need not response with the operational parameters for the connected EMD 100, but it is enough for the content server 160 to indicate, for example, the index of the database X corresponding to the connected EMD 120. In this way, the information indicating the operational attributes associated with the connected exercise monitoring device 100 may be an index of the database X stored in the computing device 120.

In step 208, the computing device 120, or more specifically the dynamic part 138 of the data processing application 134, may perform at least one operation to the exercise-related data 104 on the basis of the indicated operational attributes associated with the connected exercise monitoring device 100. Processing the exercise-related data 104 may denote processing the data in the EMD 100, in the computing device 120 and/or perform a transfer of the data 104, for example. The proposed solution may provide ease of usage from the point of view of the computing device 120 as the data processing application automatically retrieves the correct operational attributes or functional parameters needed for certain EMD 100 from the server 160.

In an embodiment, the computing device 120 acquires all of the operational attributes related to the connected EMD 100 from the server 160 substantially simultaneously. That is, even though the computing device 120 would not require any operational attributes related to handling location specific data, the computing device 120 is nevertheless provided with the attributes enabling such GPS data handling.

In another embodiment, the content of the received operational attributes are based on an explicit request from the computing device 120. That is, the content may be based on a current need and the computing device 120 may thus request the first server (160) to provide only those operational attributes which are required for forming the dynamic part 138 for a specific processing task. For example, let us assume that the first task the computing device 120 needs to do with respect to the connected EMD 100 is to transfer the data 104 to the computing device 120. Then the computing device may request the server 160 to indicate those operational parameters which are needed for the transfer, not any other operational parameters. Then, when the user 150 of the computing devise 120 or the computing device 120 itself decides that, for example, heart rate data is to be shown, the computing device 120 may request the corresponding operational parameters from the server 160.

The operational attributes (OA) may indicate at least one of the following: the types of exercise-related data available from the connected exercise monitoring device 100, a data format applied by the connected exercise monitoring device 100 for each available type of exercise-related data, coding applied by the connected exercise monitoring device 100 for each available type of exercise-related data, a communication protocol applied by the connected exercise monitoring device 100 for the transfer of the exercise-related data, identification of a second server 180 to which the exercise-related data is to be transferred. Let us look at these further.

In one embodiment, the operational attributes may indicate the types of exercise-related data available from the connected exercise monitoring device 100. This may denote that the computing device 120 may acquire knowledge of what types of exercise-related data 104 is available in the EMD 100. The computing device 120 may then process each type of data simultaneously or separately, depending on what data 104 is available. The computing device 120 may in this manner acquire knowledge of, for example, what information it should display to the user 150. If the data 104 comprise GPS location data, then the computing device 120 may show the route travelled during the physical exercise, whereas if the data 104 do not comprise such location data, then no route display needs to be generated.

In one embodiment, the operational attributes may indicate the data format and/or coding applied by the connected exercise monitoring device 100 for each available type of exercise-related data 104. In this case, the computing device 120 acquires knowledge about how the given EMD 100 connected to the computing device 120 has encoded the data 104 and in which format the data 104 is stored. By acquiring such info, the computing device 120 may perform at least one operation to the data 104, such as decoding the data 104 and displaying the data 104 to the user 150, for example.

In one embodiment, the operational attributes may indicate the communication protocol applied by the connected exercise monitoring device 100 for the transfer of the exercise-related data. The processing of the computing device 120 may in this case denote, for example, transferring the data types 104 from the EMD 100 to the computing device 120.

In one embodiment, the operational attributes may indicate the identification of a second server 180 to which the exercise-related data is to be transferred. Accordingly, the attributes may specify a specific server 180 for a given EMD 100, whereas for another type of EMD, the data server could be a different server or a target directory of the server 180 could be different. The identification of the server 180 may be the network address of the server 180, for example. Then, the computing device 120 may select the second server 180 or the target directory of the second server 180 to which the exercise-related data 104 is to be transferred at least partly on the basis of the operational attributes.

Let us look at possible ways in which the computing device 120 may, with the dynamic part 138, perform operation(s) to the exercise-related data 104. In an embodiment, the computing device 120 performs, with the dynamic part 138, at least one of the following operations: transfer the exercise-related data 104 from the connected exercise monitoring device 100 to the computing device 120, transfer the exercise-related data 104 to the second server 180 from the computing device, decode at least part of the exercise-related data 104, encode at least part of the exercise-related data 104, reorganize at least part of the exercise-related data 104, delete at least part of the exercise-related data, add information to the exercise-related data 104, display or output at least part of the exercise-related data 104, store at least part of the exercise-related data 104 to the computing device 120.

FIG. 3 shows the computing device 120 comprising the control circuitry (CTRL) 122 and the at least one memory 124 including the computer program code (PROG). The computing device 120 may be a laptop, a PC, a mobile phone, a tablet, a communicator, a smart phone, a palm computer, or any computing device. Alternatively, the computing device 120 is comprised in such a computing device. Further, the computing device 120 may be or comprise a module, to be attached to such computing device, such as a plug-in unit, an "USB dongle", or any other kind of unit.

As said, the computing device 120 may further comprise communication interface (I/O interface) 126 comprising hardware and/or software for realizing a communication connectivity according to one or more communication protocols. The interface 126 may provide the apparatus with communication capabilities to access the EMD 100 and to the network 140 (and further to the servers 160, 180), for example. The computing device 120 may also comprise the user interface (UI) 128, as indicated earlier, so that the person 150 may control the apparatus 120.

The control circuitry 122 may comprise an identifier (ID) determination circuitry 130 for determining the at least one identifier of the connected EMD 100, as explained above. The static part 136 of the data processing application 134 may apply the functionalities of the circuitry 130, for example. The control circuitry 122 may further comprise a data processing circuitry 132 responsible for performing operation(s) to the data 104 according to any of the embodiments. The dynamic part 138 of the data processing application 134 may apply the functionalities of the circuitry 132, for example.

Figure 4:
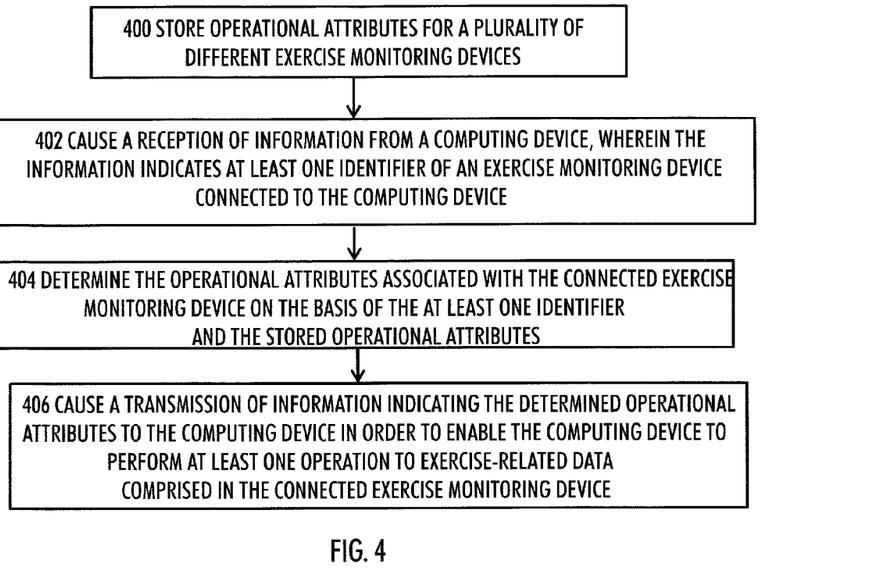
Figure 5:
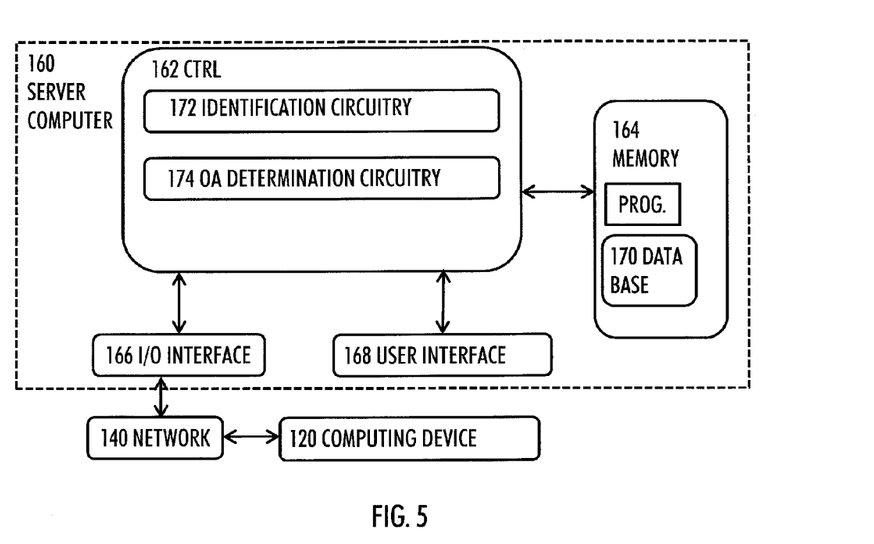

Let us look at the proposed solution from the point of view of the content server 160, which may be a server computer accessible via the network 140, with reference to FIGS. 4 and 5. FIG. 4 shows a flow diagram for the method performed by the content server 160, whereas FIG. 5 illustrates the server 160. The server 160 may comprise at least one processor 162 and at least one memory 164 including a computer program code (PROG). As shown in step 400 of FIG. 4, the at least one memory 164 and the computer program code (PROG) are configured, with the at least one processor 162, to cause the server 160 at least to store operational attributes for a plurality of different exercise monitoring devices, as mentioned earlier. The operational attribute database 170 may thus store separate data records, parameters, data structures, etc. for a plurality of different EMDs.

In step 402, the server 160 may receive information from the computing device 120, wherein the information indicates at least one identifier of the EMD 100 connected to the EMD 100.

The server 160 may then in step 404 determine the operational attributes associated with the connected EMD 100 on the basis of the at least one identifier and the stored operational attributes. For example, if it is determined on the basis of the received ID that the connected EMD 100 is the EMD #K, then the server 160 may determine that the operational attributes corresponding to the EMD #K are to be selected from the database 170 and transmitted to the device 120.

In step 406 the information indicating the determined operational attributes (corresponding to the EMD #K) is transmitted to the device 120 in order to enable the device 120 to perform at least one operation to the exercise-related data 104 comprised in the connected exercise monitoring device 100.

Let us then look at FIG. 5, which provides an embodiment illustrating the server 160 (a.k.a. the server computer 160). The server 160 comprises the CTRL 162 and the at least one memory 164. The server 160 may be a laptop, a PC, or any computing device capable of acting as a server and performing functionalities required from a server.

The apparatus may further comprise communication interface (I/O interface) 166 comprising hardware and/or software for realizing a communication connectivity according to one or more communication protocols. The interface 166 may provide the apparatus with communication capabilities to access client's device 120 via the network 140. The apparatus may also comprise a user interface (UI) 168 for controlling the server 160.

The control circuitry 162 may comprise an identification circuitry 172 for determining identity of the connected EMD 100 on the basis of the received identifier, as explained above. The control circuitry 162 may further comprise an operational attribute (OA) determination circuitry 174 responsible for determining which operational attributes are to be transmitted to the device 120 for operating with the connected EMD 100.

Figure 6:
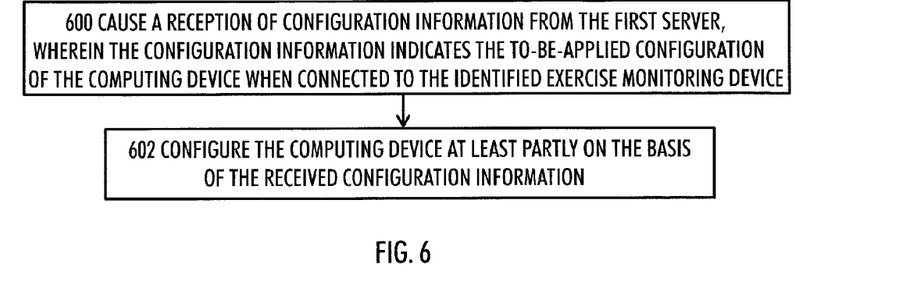

FIG. 6 depicts an embodiment in which the user's device (i.e. the computing device 120) receives in step 600 configuration information indicating the to-be-applied configuration of the computing device 120 when connected to the identified exercise monitoring device 100. The configuration data may be received from the content server 160. In step 602, the computing device 120 (e.g. the dynamic part 138) then configures itself (e.g. the data processing application 134) at least partly on the basis of the received configuration information. For example, it may be that when an EMD #C is connected to the computing device 120, the computing device 120 is required to have a certain type of configuration, whereas when an EMD #D is connected to the computing device 120, the computing device 120 or the data processing application 134 is required to have another type of configuration. The configuration information may be part of the operational attributes or it may be given as a separate data.

In an embodiment, the configuration information indicates at least one of the following: functionalities and appearance of the user interface (of the data processing application 134), language setting for the user interface, a skin or a theme of the user interface, a communication protocol to be applied for the transfer of the exercise-related data 104. For example, for a specific EMD, the user interface is required to show certain selection areas or certain information (such as the model of the connected specific EMD) in a display. In an embodiment, the language settings of the user interface may depend on the received configuration information. In an embodiment, the skin or theme of the user interface of the computing device 120 may vary depending on what type of EMD is connected and/or depending on what season (summer, winter, Christmas, Olympics, etc.) it is. Thus, the current time and/or date may affect the content of the configuration data. As an example, it may be said that such embodiment allows applying themes, such as Christmas themes or Olympic-themes, to the user interface of the computing device 120 (e.g. to the user interface of the data processing application 134 comprised in the computing device 120). The computing device 120 may in an embodiment configure its I/O interface 126 on the basis of the communication protocol which is to be applied for the transfer of the exercise-related data 104 from the EMD 100 to the computing device 120 and/or from the computing device 120 to the data server 180.

In an embodiment, the content of the received configuration information is at least partly based on at least one of the following: the identity of the computing device 120, the user 150 associated with the computing device 120. For example, when the computing device 120 is identified to be a personal home computer, such as PC, the configuration data (such as the appearance of the UI) may be different than when the computing device 120 is identified to belong to equipment of a gym, for example. Further, in an embodiment, the user 150 may affect the content of the configuration information. For example, each user 150 may have their own user profiles stored in the content server 160 and each profile may have its own visual appearance, language settings, display settings or user interface setting in general.

Figure 7:
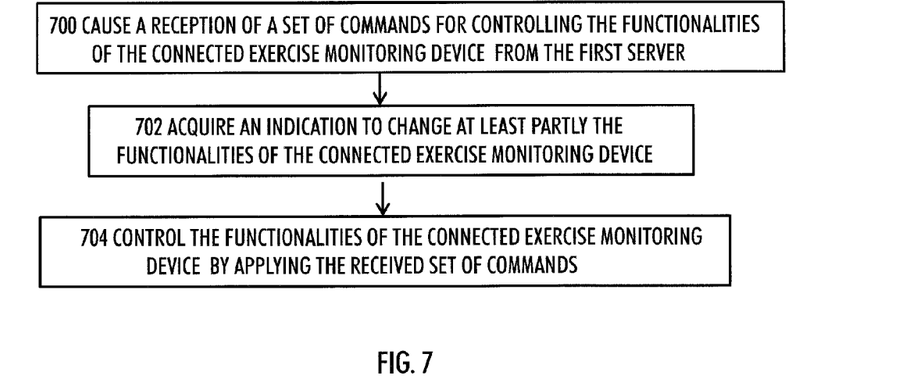

In an embodiment as shown in FIG. 7, the computing device 120 may in step 700 receive a set of commands for controlling the functionalities of the connected exercise monitoring device 120 from the content server 160. The set of commands may be part of the operational attributes indicated or the set of commands may be given as a separate data. In step 702, the computing device 100 may acquire an indication to change at least partly the functionalities of the connected exercise monitoring device 100. For example, the computing device 120 may detect that some functionalities of the EMD 100 are outdated (e.g. the firmware is old) or the user 150 may indicate that, e.g. at least one training display needs to be amended. Consequently, in step 704 the computing device 120 may, with the dynamic part 138, control the functionalities of the connected exercise monitoring device 100 by applying the received set of commands. For example, the user 150 may define a new training display is needed for running-exercises. The user 150 and the computing device 120 may then add such new training display to the connected EMD 100 on the basis of the received set of commands corresponding to the currently connected EMD 100. Each EMD may have its own set of commands. Therefore, it may be beneficial not to store sets of commands for a plurality of EMDs in the memory 124 but to request the to-be-applied set of commands corresponding to the currently connected EMD from the server 160.

Figure 8:
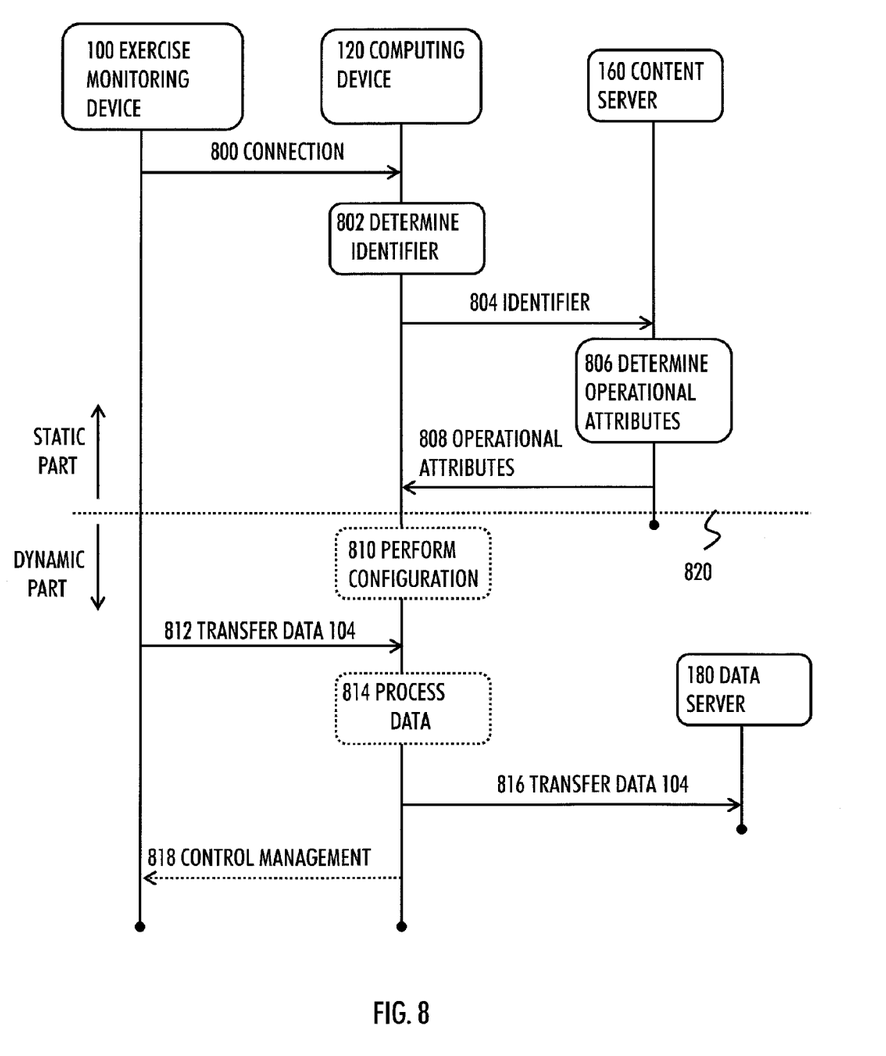
FIG. 8 illustrate a signaling flow diagram according to an embodiment.

FIG. 8 shows a signaling flow diagram with respect to the proposed system. In step 800 the EMD 100 is connected to the client's device (e.g. the computing device) 120. In step 802, the computing device 120 defines at least one identifier of the EMD 100 and transmits it to the content server 160 in step 804. Optionally, the computing device 120 may identify the EMD on the basis of the identifier. In step 806 the content server 160 selects the operational attributes corresponding to the connected EMD 100 on the basis of the identifier. The operational attributes are selected from a set of operational attributes stored in the database 170, each set corresponding to a different type of exercise monitoring device. Thereafter, in step 808 the content server 160 indicates the operational attributes to the computing device 120. Alternatively, the content server 160 may indicate the index for the correct operational attributes when the computing device 120 itself stores such set of operational attributes, each set corresponding to a different type of exercise monitoring device.

In an optional step 810 the computing device 120 may perform (re)configuration of its own user interface, communication protocols, etc. on the basis of the configuration information, as explained earlier. In step 812, the computing device 120 may transfer the data 104 from the EMD 100 to the computing device 120. In an optional step 814 the computing device 120 may perform further processing to the data, such as storing the data 104, adding information elements to the data 104, etc., as explained earlier. In step 816, the computing device 120 may transfer the data 104 to the data server 180. In an optional step 818 the computing device 120 may control the functionalities of the EMD 100 on the basis of received set of commands, as explained earlier.

As shown in FIG. 8, the static part 136 of the data processing application 134 may be responsible of performing the tasks which are above a horizontal dotted line 820. The tasks which are below the horizontal dotted line 820 may be tasks performed by the dynamic part 138 of the data processing application.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

The invention claimed is:

1. A server computer, comprising:
at least one processor and at least one memory including a computer program code, wherein the at least one memory and the computer program code are configured, with the at least one processor, to cause the server computer to perform operations comprising:
storing operational attributes for a plurality of different exercise monitoring devices;
causing a reception of information from a static part of a data processing application of a computing device applied by a user, wherein the information indicates at least one identifier of an exercise monitoring device connected to the computing device, an identity of the connected exercise monitoring device determined using an identification circuitry;
determining, using an operational attribute determination circuitry, determined operational attributes associated with the connected exercise monitoring device on the basis of the at least one identifier and the stored operational attributes; and
causing a transmission of information indicating the determined operational attributes to the computing device, wherein the determined operational attributes indicate at least an identification of a second server or a target directory of the second server to which exercise-related data is to be transferred, in order to enable the computing device to transfer the exercise-related data from the connected exercise monitoring device to the computing device and to transfer the exercise-related data from the computing device to the second server.

2. The server computer of claim 1, wherein the determined operational attributes comprise an executable packet which auto-generate a dynamic part to the data processing application of the computing device.

3. The server computer of claim 1, wherein the identifier comprises at least one of the following with respect to the connected exercise monitoring device: a type identifier, a model identifier, the serial number, an age identifier, a manufacturer identifier, a firmware version identifier.

4. The server computer of claim 1, wherein the at least one memory and the computer program code are configured, with the at least one processor, to cause the server computer to
receive a request from the computing device to indicate the determined operational attributes associated with the connected exercise monitoring device on the basis of the at least one identifier each time upon connection of any exercise monitoring device to the computing device.

5. The server computer of claim 1, wherein the operational attributes indicate the types of exercise-related data available from the connected exercise monitoring device.

6. The server computer of claim 1, wherein the operational attributes indicate at least one of the following: a data format applied by the connected exercise monitoring device for each available type of exercise-related data, coding applied by the connected exercise monitoring device for each available type of exercise-related data, a communication protocol applied by the connected exercise monitoring device for the transfer of the exercise-related data.

7. The server computer of claim 1, wherein the types of exercise-related data available from the connected exercise monitoring device comprise location specific exercise data.

8. The server computer of claim 1, wherein the types of exercise-related data available from the connected exercise monitoring device comprise activity information.

9. The server computer of claim 1, wherein the types of exercise-related data available from the connected exercise monitoring device comprise at least one of the following: heart rate zones, heart rate samples, heart rate variation samples, fat consumption, calorie consumption, activity zones, activity samples, speed and/or pace samples, power samples, cadence samples, altitude samples, temperature samples, location samples, pedal index, left-right balance, running index, training load, galvanic skin response samples, fluid balance, skin temperature samples, music samples.

10. The server computer of claim 1, wherein the transmitted information indicating the determined operational attributes enable the computing device to further perform at least one of the following operations to the exercise-related data:
decode at least part of the exercise-related data, encode at least part of the exercise-related data, reorganize at least part of the exercise-related data, delete at least part of the exercise-related data, add information to the exercise-related data, display or output at least part of the exercise-related data, store at least part of the exercise-related data to the computing device.

11. The server computer of claim 1, wherein the at least one memory and the computer program code are configured, with the at least one processor, to cause the server computer to
cause a transmission of configuration information to the computing device, wherein the configuration information indicates the to-be-applied configuration of the computing device when connected to the identified exercise monitoring device in order to enable the computing device to configure the computing device at least partly on the basis of the transmitted configuration information, wherein the configuration information indicates at least one of the following: functionalities and appearance of the user interface, language setting for the user interface, a skin or a theme of the user interface, a communication protocol to be applied for the transfer of the exercise-related data.

12. The server computer of claim 11, wherein the content of the received configuration information is at least partly based on the identity of the computing device and/or the identity of the user associated with the computing device.

13. The server computer of claim 1, wherein the at least one memory and the computer program code are configured, with the at least one processor, to cause the server computer to
cause a transmission of a set of exercise monitoring device-specific commands to the computing device in order to allow the computing device to control the functionalities of the connected exercise monitoring device by applying the transmitted set of commands.

14. A method, comprising:
storing, by a server computer, operational attributes for a plurality of different exercise monitoring devices;
receiving information from a static part of a data processing application of a computing device applied by a user, wherein the information indicates at least one identifier of an exercise monitoring device connected to the computing device;
determining determined operational attributes associated with the connected exercise monitoring device on the basis of the at least one identifier and the stored operational attributes; and
transmitting information indicating the determined operational attributes to the computing device, wherein the determined operational attributes indicate at least an identification of a second server or a target directory of the second server to which exercise-related data is to be transferred, in order to enable the computing device to transfer the exercise-related data from the connected exercise monitoring device to the computing device and to transfer the exercise-related data from the computing device to the second server.

15. A computer program product embodied on a distribution medium readable by a computer and comprising program instructions which, when loaded into an apparatus, cause the apparatus to execute at least the following:
storing, by a server computer, operational attributes for a plurality of different exercise monitoring devices;
receiving information from a static part of a data processing application of a computing device applied by a user, wherein the information indicates at least one identifier of an exercise monitoring device connected to the computing device;
determining determined operational attributes associated with the connected exercise monitoring device on the basis of the at least one identifier and the stored operational attributes; and
transmitting information indicating the determined operational attributes to the computing device, wherein the determined operational attributes indicate at least an identification of a second server or a target directory of the second server to which exercise-related data is to be transferred, in order to enable the computing device to transfer the exercise-related data from the connected exercise monitoring device to the computing device and to transfer the exercise-related data from the computing device to the second server.

16. A computing device, comprising:
at least one processor and at least one memory including a computer program code, wherein the at least one memory and the computer program code are configured, with the at least one processor, to cause the computing device to perform operations comprising:
executing, in the computing device, a data processing application comprising a static part for performing at least the following functions when an exercise monitoring device is connected to the computing device:
determining at least one identifier of the connected exercise monitoring device, an identity of the connected exercise monitoring device determined using an identification circuitry, wherein the connected exercise monitoring device comprises exercise-related data;
causing an indication of the determined at least one identifier to a first server over a network, wherein the first server stores operational attributes for a plurality of different exercise monitoring devices; and
causing a reception of information indicating indicated operational attributes associated with the connected exercise monitoring device from the first server, wherein the indicated operational attributes form an exercise monitoring device specific dynamic part of the data processing application, and the computing device is further caused to perform operations comprising:
performing, with the dynamic part, at least one operation to the exercise-related data on the basis of the indicated operational attributes associated with the connected exercise monitoring device, wherein the indicated operational attributes indicate at least an identification of a second server or a target directory of the second server to which the exercise-related data is to be transferred, and the computing device is further caused to perform operations comprising:
transferring the exercise-related data from the connected exercise monitoring device to the computing device; and
transferring the exercise-related data from the computing device to the second server.

17. The computing device of claim 16, wherein the static part performs at least the said functions each time any exercise monitoring device is connected to the computing device.

18. The computing device of claim 16, wherein the at least one memory and the computer program code are configured, with the at least one processor, to cause the computing device to perform operations comprising:
causing a reception of a set of commands for controlling the functionalities of the connected exercise monitoring device from the first server;
acquiring an indication to change at least partly the functionalities of the connected exercise monitoring device; and
controlling the functionalities of the connected exercise monitoring device by applying the received set of commands.

* * * * *

UNITED STATES PATENT AND TRADEMARK OFFICE
CERTIFICATE OF CORRECTION

PATENT NO. : 9,700,760 B2
APPLICATION NO. : 14/095552
DATED : July 11, 2017
INVENTOR(S) : Poyhtari et al.

Page 1 of 1

It is certified that error appears in the above-identified patent and that said Letters Patent is hereby corrected as shown below:

In the Specification

Column 3, Line 67: now reads "at least one the following"
should read -- at least one of the following --

Column 5, Line 49: now reads "with respect the currently"
should read -- with respect to the currently --

Signed and Sealed this
Twentieth Day of February, 2018

Andrei Iancu
*Director of the United States Patent and Trademark Office*